US006482435B1

(12) United States Patent
Stratton et al.

(10) Patent No.: US 6,482,435 B1
(45) Date of Patent: Nov. 19, 2002

(54) TEMPERATURE SENSITIVE GEL FOR SUSTAINED DELIVERY OF PROTEIN DRUGS

(75) Inventors: Lewis P. Stratton, Greenville, SC (US); John F. Carpenter, Littleton, CO (US); Mark C. Manning, Fort Collins, CO (US)

(73) Assignee: University Technology Corporation, Boulder, CO (US)

(*) Notice: Subject to any disclaimer, the term of this patent is extended or adjusted under 35 U.S.C. 154(b) by 0 days.

(21) Appl. No.: 09/232,288

(22) Filed: Jan. 15, 1999

Related U.S. Application Data

(62) Division of application No. 08/679,199, filed on Jul. 12, 1996, now Pat. No. 5,861,174.

(51) Int. Cl.[7] .......................... A61K 9/10; A61K 47/34; A61K 47/26
(52) U.S. Cl. .................. 424/486; 514/944; 516/105
(58) Field of Search .................. 424/484, 486–488; 514/944; 516/104–105

(56) References Cited

U.S. PATENT DOCUMENTS

| | | | |
|---|---|---|---|
| 4,100,271 A | * 7/1978 | Krezanoski | |
| 4,188,373 A | 2/1980 | Krezanoski | 424/78 |
| 4,465,622 A | 8/1984 | Nobuhara et al. | 260/112 |
| 4,474,751 A | 10/1984 | Haslam et al. | 424/78 |
| 4,474,752 A | 10/1984 | Haslam et al. | 424/78 |
| 4,474,753 A | 10/1984 | Haslam et al. | 424/78 |
| 4,478,822 A | 10/1984 | Haslam et al. | 424/78 |
| 4,702,917 A | 10/1987 | Schindler | 424/422 |
| 4,895,716 A | 1/1990 | Goldstein et al. | 424/85.5 |
| 4,925,677 A | 5/1990 | Feijen | 424/484 |
| 4,954,154 A | * 9/1990 | Gogrtz | |
| 4,962,091 A | 10/1990 | Eppstein et al. | 514/2 |
| 5,041,292 A | 8/1991 | Feijen | 424/484 |
| 5,071,644 A | 12/1991 | Viegas et al. | 514/772.7 |
| 5,077,033 A | 12/1991 | Viegas et al. | 514/668 |
| 5,124,151 A | 6/1992 | Viegas et al. | 424/422 |
| 5,126,141 A | 6/1992 | Henry | 424/423 |
| 5,143,731 A | 9/1992 | Viegas et al. | 424/486 |
| 5,229,469 A | 7/1993 | Krone et al. | 525/420 |
| 5,292,516 A | 3/1994 | Viegas et al. | 424/423 |
| 5,300,295 A | 4/1994 | Viegas et al. | 424/427 |
| 5,306,501 A | 4/1994 | Viegas et al. | 424/423 |
| 5,328,695 A | 7/1994 | Lucas et al. | 424/426 |
| 5,330,768 A | 7/1994 | Park et al. | 424/501 |
| 5,346,703 A | 9/1994 | Viegas et al. | 424/486 |
| 5,411,737 A | 5/1995 | Hsu et al. | 424/411 |
| 5,420,197 A | 5/1995 | Lorenz et al. | 525/54.3 |
| 5,427,778 A | 6/1995 | Finkenaur et al. | 424/78.08 |
| 5,446,023 A | 8/1995 | Pavia et al. | 514/12 |
| 5,457,093 A | 10/1995 | Cini et al. | 514/12 |
| 5,468,505 A | 11/1995 | Hubbell et al. | 424/484 |
| 5,554,147 A | * 9/1996 | Batich et al. | |
| 5,589,167 A | 12/1996 | Cleland et al. | 424/85.7 |

OTHER PUBLICATIONS

Arakawa, *Pharmaceutical Research*, 8:285–291 (1991).

(List continued on next page.)

*Primary Examiner*—Edward J. Webman
(74) *Attorney, Agent, or Firm*—Sheridan Ross P.C.

(57) ABSTRACT

Pharmaceutical compositions for the delivery of pharmacologically active proteins are provided by the present invention. The compositions of the present invention comprise a polymeric matrix having thermal gelation properties in which is incorporated a discrete suspension of at least one biologically active macromolecular polypeptide which retains greater than 90 percent of its biological activity. Furthermore, the concentration of the macromolecular polypeptide is greater than 0.5 percent by weight of the composition.

10 Claims, 1 Drawing Sheet

OTHER PUBLICATIONS

"Sustained Delivery of Interleukin–2 from a Poloxamer 407 Gel Matrix Following Intraperitioneal Injection in Mice," Johnston, Punjabi and Froelich, *Pharmaceutical Research*, 9(3):425–434 (1992).

"Biological Activity of Urease Formulated in Poloxamer 407 after Intraperitoneal Injection in the Rat," Pec, Wout and Johnston, *Journal of Pharmaceutical Sciences*, 18(7):626–630 (1992).

"Sustained–release interleukin–2 following intramuscular injection in rats," Wang and Johnston, *International Journal of Pharmaceutics* 113:73–81 (1995).

"Enhanced Stability of Two Model Proteins in an Agitated Solution Environment Using Poloxamer 407," Wang and Johnston, *Journal of Parenteral Science & Technology*, 47(4):183–189 (1993).

"Thermal–induced denaturation of two model proteins: effect of poloxamer 407 on solution stability," Wang and Johnston, *International Journal of Pharmaceutics*, 96:41–49 (1993).

* cited by examiner

TEMPERATURE SENSITIVE GEL FOR SUSTAINED DELIVERY OF PROTEIN DRUGS

CROSS-REFERENCE TO OTHER APPLICATIONS

This patent application is a divisional of application Ser. No. 08/679,199, filed Jul. 12, 1996 now U.S. Pat. No. 5,861,174 entitled "Temperature Sensitive Gel For Sustained Delivery of Protein Drugs."

BACKGROUND OF THE INVENTION

1. Field of the Invention

The present invention relates to temperature-sensitive polymers for the sustained delivery of pharmacological agents and, more particularly, to poloxamers comprising suspensions of native macromolecular polypeptide agents.

2. Description of the State of the Art

Recent years have seen major advances in recombinant DNA techniques and consequently the proliferation of many protein pharmaceuticals available for a variety of therapeutic needs. Indeed, proteins or polypeptides constitute the largest class of drugs currently being considered for FDA approval. However, the therapeutic and commercial potential of polypeptide drugs will only be realized if these advances are accompanied by formulation designs leading to effective administration and stability.

Proteins are large organic molecules or macromolecules made up of amino acid residues covalently linked together by peptide bonds into a linear, unbranched polypeptide chain with relative molecular mass ranging from a few thousand to millions. The useful properties of proteins as drugs depend upon the polypeptide chain adopting a unique three-dimensional folded conformation, that is, the tertiary structure of the protein. It is this unique folding that is responsible for the protein being highly selective in the molecules it will recognize. However, the ability to maintain a unique three-dimensional structure is precisely one of the obstacles that makes the use of polypeptides in human and animal diseases fraught with problems.

Traditionally, the most widely used method of administration of therapeutic agents is by the oral route. However, such delivery is not feasible, in the case of macromolecular drugs, as they are rapidly degraded and deactivated by hydrolytic enzymes in the alimentary tract. Even if stable to enzymatic digestion, their molecular weights are too high for absorption through the intestinal wall. Consequently, they are usually administered parenterally; but, since such drugs often have short half-lives in vivo, frequent injections are required to produce an effective therapy. Unfortunately, while the parenteral route is the most efficient means of drug introduction, this route has severe drawbacks in that injections are painful; they can lead to infection; and they can lead to severe vascular problems as a result of repeated intravenous injections.

For these reasons, biodegradable polymer matrices have been considered as sustained release delivery systems for a variety of active agents or drugs. Once implanted, the matrix slowly dissolves or erodes, releasing the drug. An alternative approach is to use small implantable pumps, which slowly extrude the drug and matrix components, which dissolve after contacting body fluids. With both systems it is crucial that the drug remain evenly distributed throughout the matrix since heterogeneous distribution of the drug (e.g., formation of large clumps and voids) could lead to erratic dosing. Furthermore, both systems require polymers that remain somewhat fluid so that they can be easily manipulated prior to implantation or loading into a device.

The use of polymers as solid implants and for use in small implantable pumps for the delivery of several therapeutic agents has been disclosed in scientific publications and in the patent literature. See, for example, Kent, et al., "In vivo controlled release of an LHRH analog from injected polymeric microcapsules", *Contracept, Deliv. Syst.*, 3:58 (1982); Sanders, et al., "Controlled release of a luteinizing hormone releasing hormone analogue from poly (d, 1-lactide-co-glycolide)—microspheres", *J. Pharmaceut. Sci.*, 73:1294–1297 (1984); Johnston, T. P., et al., "Sustained delivery of Interleukin-2 from a poloxamer 407 gel matrix following intraperitoneal injection in mice", *Pharmaceut. Res.*, 9(3):425–434 (1992); Yolks, et al., "Timed release depot for anti-cancer agents II", *Acta Pharm. Svec.*, 15:382–388 (1978); Krezanoski, "Clear, water-miscible, liquid pharmaceutical vehicles and compositions which gel at body temperature for drug delivery to mucous membranes", U.S. Pat. No. 4,474,752. However, the polymers having the greatest potential for use in the delivery of protein drugs would exhibit reverse thermal gelation and have good drug release characteristics.

There exists a class of block copolymers that may be generically classified as polyoxyethylene-polyoxypropylene condensates, namely Pluronic polyols, or poloxamers. They are formed by the condensation of propylene oxide into a propylene glycol nucleus followed by the condensation of ethylene oxide into both ends of the polyoxypropylene base. The polyoxyethylene hydrophilic groups on the ends of the molecule are controlled in length to constitute anywhere from 10 percent to 80 percent by weight of the final molecule.

Poloxamers, which have the ability to gel as a function of temperature and polymer concentration, may be represented emperically by the formula:

$$HO(C_2H_4O)_b(C_3H_6O)_a(C_2H_4O)_bH \qquad (I)$$

wherein a and b are integers such that the hydrophobe base represented by $(C_3H_6O)_a$ has a molecular weight ranging from about 900 to 4,000, as determined by hydroxyl number; and the polyoxyethylene chain consisting of at least 60 percent to 70 percent by weight of the copolymer, and the copolymer having a total average molecular weight ranging from about 4,000 to 15,000. Table 1, below, references the minimum concentrations of various poloxamers necessary to form a gel in water at room temperature.

TABLE 1

| Poloxamer* | Molecular Weight | Minimum Concentration |
|---|---|---|
| Pluronic ® F-68 | 8,400 | 50%–60% |
| Pluronic ® F-88 | 11,400 | 40% |
| Pluronic ® F-108 | 14,600 | 30% |
| Pluronic ® F-127 | 12,600 | 20% |

*Poloxamers are commercially available under the referenced trademarks through the BASF Corporation, Parsippany, N.J.

Poloxamers of low molecular weight, i.e., below 10,000 MW, do not form gels at any concentration in water.

While poloxamers, and more specifically Pluronic® F-127 or Poloxamer 407, have been used to deliver non-peptidic drugs as well as biologically active proteins, see U.S. Pat. Nos. 4,100,271 and 5,457,093, respectively, sustained delivery of biologically active macromolecules for weeks or months has not been possible for reasons that are two-fold. First, previous references which disclose the incorporation of proteins in a Pluronic® matrix only disclose solutions of a protein, with concentrations less than approximately 2 mg/ml and second, formulation approaches used to incorporate proteins into polymeric systems often result in irreversible inactivation of the proteins because of the presence of organic solvents, pH changes, and thermal effects. Consequently, prior references which teach the use of poloxamers as pharmaceutical vehicles for the delivery of proteins have suffered two serious limitations; (i) low initial concentrations of protein are used, and (ii) an unacceptable percentage of the protein loses its biological activity during use or storage. These two limitations have a direct impact on the ability to produce a polypeptide drug delivery system which can be shelved for long periods of time prior to usage and administer controlled dosages of protein for a period of weeks or more preferably months. Furthermore, degraded proteins can have reduced efficacy as a drug, and can also elicit adverse reactions, such as sensitization and adverse immune response.

There is still a need, therefore, for a polypeptide drug delivery device or composition having high concentrations of fully native macromolecular polypeptides which may be regularly released over a long period of time.

SUMMARY OF THE INVENTION

Accordingly, it is an object of this invention to provide a polypeptide drug delivery system.

It is a further object of this invention to provide a polypeptide drug delivery device or composition having protein or peptide concentrations greater than 5 mg/ml.

It is an additional object of the present invention to incorporate protein stabilizers into the drug delivery device.

Additional objects, advantages and novel features of this invention shall be set forth in part in the description that follows, and in part will become apparent to those skilled in the art upon examination of the following specification or may be learned by the practice of the invention. The objects and advantages of the invention may be realized and attained by means of the instrumentalities, combinations, compositions, and methods particularly pointed out in the appended claims.

To achieve the foregoing and other objects and in accordance with the purposes of the present invention, as embodied and broadly described therein, the composition of the present invention comprises a polymeric matrix having thermal gelation properties in which is incorporated a suspension of at least one biologically active macromolecular polypeptide having a concentration of 0.5 percent or greater by weight of the composition.

BRIEF DESCRIPTION OF THE DRAWING

The accompanying drawing, which is incorporated in and forms a part of the specification, illustrates the prepared embodiments of the present invention, and together with the description serves to explain the principles of the invention.

In the Drawing.

Figure 1:
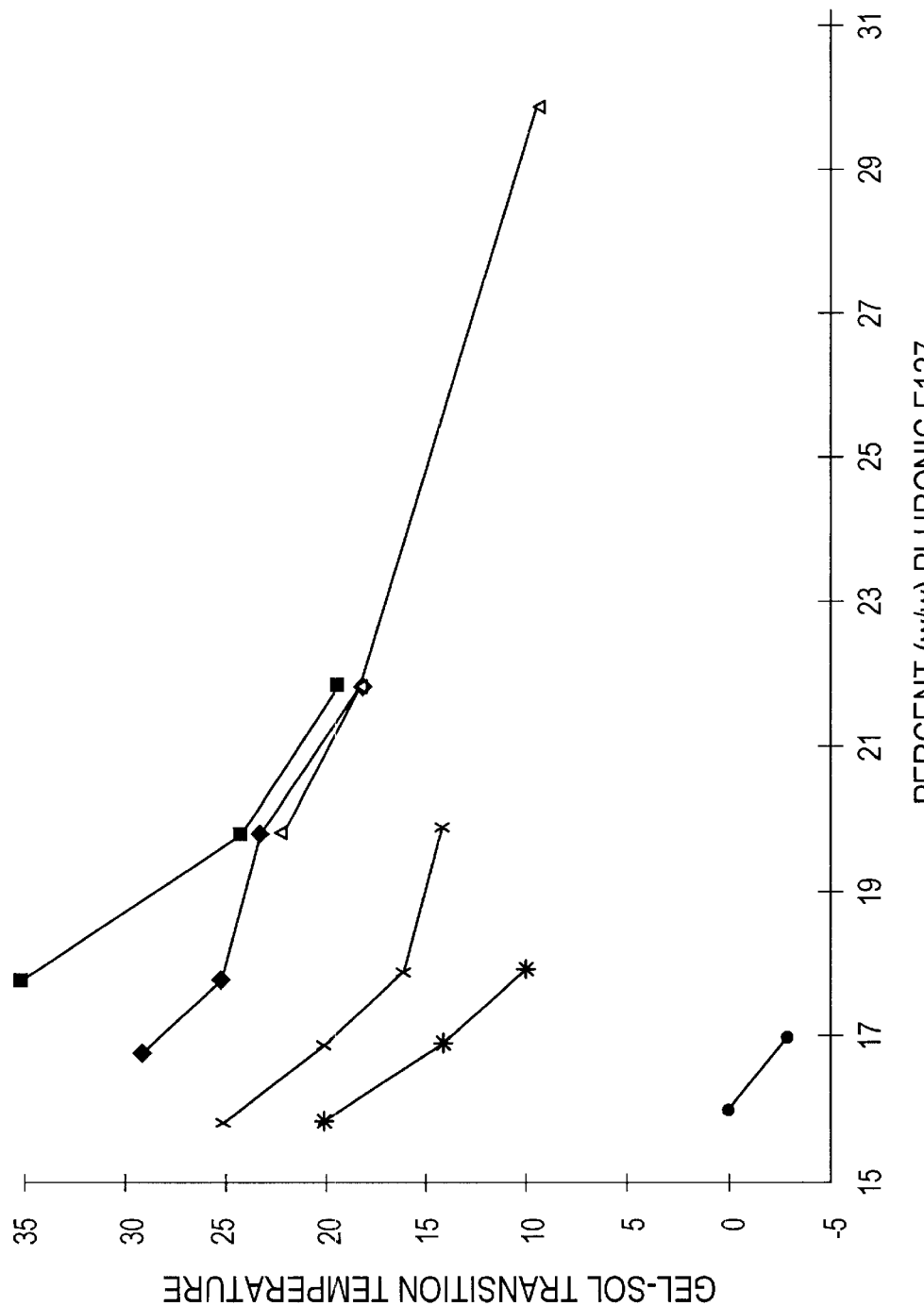
FIG. 1 is a graphic representation of the effects various additives have on the solution-gel (sol-gel) transition temperature of the present invention, wherein each additive is represented by the following symbols.

-◆- 0.1% PEG 800, -x- 0.5 M Sucrose, -■- 1.0% PEG 800, -*- 1.0 M Sucrose, -Δ- Pluronic® F-127, -●- 1.5 M Sucrose.

DETAIL DESCRIPTION OF THE PREFERRED EMBODIMENT

The pharmaceutical device or composition of the present invention provides a delivery system for the controlled and sustained administration of fully native macromolecular polypeptides or therapeutic agents to a human or animal. The biodegradable, biocompatible matrix for drug delivery is formed by suspending soluble and insoluble particles of fully native macromolecular polypeptides having a concentration of 5 mg/ml or greater, and other protein stabilizing components uniformly and discretely throughout a pharmaceutical vehicle or polymer matrix that exhibits reverse thermal gelation characteristics. As with previously known systems, the suspended particles and other components are released through a combination of diffusion and dissolution mechanisms as the device hydrates and subsequently erodes or dissolves. However, unlike known polymeric matrix systems which deliver macromolecules, the composition of this invention comprises a suspension as opposed to a solution of native polypeptide(s). Consequently, high polypeptide concentrations are attained as a result of the suspension, thus achieving the ability for sustained administration of the therapeutic agent for a time period of days, weeks or months as opposed to hours. Furthermore, stabilizing agents may be incorporated into the composition of the present invention thereby further minimizing the degradation of these drugs, which directly impacts the efficacy of the drug and the ability to store or ship the device to worldwide markets.

The pharmaceutical composition of the present invention is a serendipitous discovery that was made during a research project, the goal of which was simply to identify a drug delivery system that was amenable to study the effect of polymeric matrices on protein structure. In that study, Fourier transform infrared spectroscopy was employed, because it can be used to analyze protein secondary structure in solutions, suspensions, and solids. Of the various protein drug delivery matrices disclosed in the literature, those employing the polymeric detergent, Pluronic® F-127, which forms a temperature sensitive gel, were the most attractive for infrared spectroscopic studies, as it did not appear (based on the structures of poloxamer) that poloxamers would have an infrared absorbance that would interfere with the protein absorbance signal, which is needed for structural evaluation. Furthermore, it had previously been established that poloxamers, at sufficient concentrations, have the characteristics of being liquid at temperatures below room temperature but will form into gel as they are warmed. Thus, a further objective of the study was to determine what effect this liquid to gel transition of the poloxamer would have on the protein's structure. In order to study protein structure with infrared spectroscopy it is necessary to have protein concentrations of at least 15–20 mg/ml, thus a protein concentration of 20 mg/ml was prepared in the presence of sufficient poloxamer to allow gelling during warming. The resulting protein solution formed a fine, milky suspension, which was initially very disappointing, because the formation of such suspensions often indicates that a solution component (e.g., the polymeric detergent) caused the protein to denature and to form non-native or inactive protein aggregates, thus indicating failure of the test. However, infrared spectroscopy can, fortunately, be used to analyze protein structures in suspension, so the suspension was analyzed anyway. Surprisingly, when the protein suspension was analyzed with the Fourier transform infrared spectroscopy, instead of finding the expected non-native or inactive protein aggregates, it was unexpectedly found to be fully native.

In accordance with the present invention, the pharmaceutical composition of the present invention comprises a polymer such as a polyoxyalkylene block copolymer of formula:

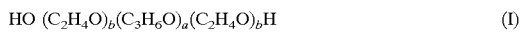

$$HO\ (C_2H_4O)_b(C_3H_6O)_a(C_2H_4O)_bH \tag{I}$$

which has the unique feature, in the preferred embodiment, of being liquid at ambient or lower temperatures and existing as a semi-solid gel at mammalian body temperatures wherein a and b are integers in the range of 20 to 80 and 15 to 60, respectively. A preferred polyoxyalkylene block copolymer for use as the pharmaceutical vehicle of this invention is a polyoxyethylene-polyoxypropylene block copolymer having the following formula:

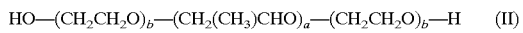

$$HO\text{—}(CH_2CH_2O)_b\text{—}(CH_2(CH_3)CHO)_a\text{—}(CH_2CH_2O)_b\text{—}H \tag{II}$$

wherein a and b are integers such that the hydrophobe base represented by $(CH_2(CH_3)CHO)_a$ has a molecular weight of at least about 4,000, as determined by hydroxyl number; the polyoxyethylene chain constituting about 70 percent of the total number of monomeric units in the molecule and where the copolymer has an average molecular weight of about 12,600. Pluronic® F-127, also known as Poloxamer 407, is such a material.

The procedures used to prepare aqueous solutions which form gels of polyoxyalkylene block copolymer are well known. For example, either a hot or cold process for forming the solutions can be used. The cold technique involves the steps of dissolving the polyoxalkylene block copolymer at a temperature of about 5° C. to 10° C. in water or in a buffer, such as a phosphate buffer. The water, if used in forming the aqueous solution, is preferably purified, as by distillation, filtration, ion-exchange or the like. When the solution is complete it is brought to room temperature whereupon it forms a gel. If the hot process of forming the gel is used, the polymer is added to water or a buffer and heated to a temperature of about 75° C. to 85° C. with slow stirring until a clear homogenous solution is obtained, upon cooling a clear gel forms.

Any macromolecular polypeptide may be mixed with the pharmaceutical vehicle to form the pharmaceutical composition of this invention wherein the concentration of macromolecular polypeptide is in the range of 0.5 to 50 percent by weight of the composition. The choice of polypeptides which can be delivered in accordance with the practice of this invention is limited only by the requirement that they be at least very slightly soluble in an aqueous physiological media such as plasma, interstitial fluid, and the intra and extracellular fluids of the subcutaneous space and mucosal tissues.

Exemplary classes of polypeptides include, among others, proteins, enzymes, nucleoproteins, glycoproteins, lipoproteins, hormonally active polypeptides, and synthetic analogues including agonists and antagonists of these molecules.

Specific examples of polypeptides suitable for incorporation in the delivery system of the present invention include the following biologically active macromolecules: interferons, interleukins, insulin, enzyme inhibitors, colony-stimulating factors, plasminogen activators, growth factors and polypeptide hormones.

The list of macromolecular polypeptides recited above are provided only to illustrate the types of active agents which are suitable for use in practicing the present invention, and are not intended to limit the scope of the present invention.

The pharmaceutical composition of the present invention can be readily prepared using any solution forming technique which achieves the concentration of polyoxyalkylene block copolymer necessary for gelling. Preferably the pharmaceutical vehicle and polypeptide mixture are prepared separately and the polypeptide mixture having a concentration of 5 mg/ml or greater is added thereto at a temperature of about 0° C. to 10° C. When combined the protein forms a homogenous suspension of fine particles in the polymer solution, which then has a "milky" appearance. By light microscopy the particles are approximately 5–10 microns in diameter. Raising the sample temperature above the gel point of the poloxamer results in an even distribution of protein particles throughout the polymer gel. Due to the high viscosity of the gel matrix, the particles remain homogeneously distributed and do not "settle out." The liquid to gel transition is fully reversible upon cooling. Furthermore, when the gel is exposed to an aqueous solution, the gel matrix and protein particles dissolve, releasing the fully native protein which retains greater than 90 percent of its biological activity.

The pharmaceutical composition of the present invention can be implanted directly into the body by injecting it as a liquid, whereupon the pharmaceutical composition will gel once inside the body. In the alternative, the pharmaceutical composition may be introduced into a small implantable pump which is then introduced into the body.

In another embodiment, protein-stabilizing solutes, can be incorporated into the pharmaceutical device of the present invention described above. Initially, stabilizers were added to the pharmaceutical device of the present invention to increase the stability of the macromolecular polypeptides as such stabilization would be crucial for use of the present invention for sustained delivery of protein in the body. However, in doing so it was discovered that protein-stabilizing solutes, such as sucrose not only aid in protecting and stabilizing the protein, but also allow the poloxamer to form suitable gels at lower concentrations than needed in water or buffer alone. Thus, the working range of polymer concentration can be widened. As discussed previously, the concentration of the polyoxyalkylene block copolymer is an important parameter. It is known that a gel will not form when the concentration of polyoxyalkylene-polyoxypropylene block copolymer in water or dilute buffer is outside of the range of about 20 to 30 percent by weight, as shown in FIG. 1 and exemplified by the line having open triangles. However, by introducing protein-stabilizing solutes to the pharmaceutical device of the present invention the gel-sol transition temperature may be manipulated, while also lowering the concentration of polyoxyethelene-polyoxypropylene block copolymer which is necessary to form a gel.

In a third embodiment, polypeptide concentrations at the high end of the 0.5 to 50 percent by weight range can be achieved by centrifuging the pharmaceutical composition of the present invention at low temperatures in the range of −10° C. to 10° C., and preferably 0–4° C. for a period of time sufficient to sediment the protein particles. For example, a sample of the pharmaceutical composition described previously comprising 20 mg/ml protein can be centrifuged at 4° C. so that the insoluble protein particles sediment. Then supernatant equivalent to half the volume could be removed and the sediment resuspended in the remaining liquid. This will result in a suspension containing almost 40 mg/ml.

In the Examples which follow the pharmaceutical composition of the present invention was prepared according to the following preparation procedure. Since the polyoxyalkylenes dissolve more completely at reduced temperatures, the preferred methods of solubilization are to add the required amount of copolymer to the amount of water or buffer to be used. Generally after wetting the copolymer by shaking, the mixture is capped and placed in a cold chamber or in a thermostatic container at about 0° C. to 10° C. in order to dissolve the copolymer. The mixture can be stirred or shaken to bring about a more rapid solution of the polymer. The polypeptides and various additives such as stabilizers can subsequently be added and dissolved to form a suspension.

The following non-limited examples provide methods for preparing temperature sensitive polymers for the sustained delivery of pharmaceutical agents comprising high concentrations of fully native macromolecular polypeptide agents. All scientific and technical terms have the meanings as understood by one with ordinary skill in the art. The specific examples which follow, illustrate the representative polypeptides and concentrations capable of being achieved by the present invention and are not to be construed as limiting the invention in sphere or scope. The methods may be adapted to variation in order to produce compositions or devices embraced by this invention but not specifically disclosed. Further variations of the methods to produce the same compositions in somewhat different fashion will be evident to one skilled in the art.

All temperatures are understood to be in Centigrade (°C.) when not specified. The infrared (IR) spectral description was measured on a Nicolet Magna-IR 550 Spectrometer. Commercially available chemicals were used without purification.

In the Examples which follow the 27.5 percent (w/w) solution of Pluronic® F-127 was prepared in the following manner. 7.59 grams of dry Pluronic® F-127was added to a sterile tube containing 20 grams of an ice cold phosphate buffer (pH 7.4, 30 mM). The tube was capped and the mixture was well shaken prior to being stored overnight at 4° C.

EXAMPLE 1

Preparation and Characterization of a Suspension of Chymotrypsin in Pluronic® F-127 a) Preparation of the Suspension

When 50 μL of a 100 mg/mL suspension of chymotrypsin in 30 mM phosphate buffer at pH 7.4 were mixed with 200 μL of a 27.5 percent (w/w) solution of Pluronic® F-127 at 4° C. a white, uniform, milky suspension formed immediately. The suspension contained 20 mg/mL protein and 22 percent (w/w) Pluronic® F-127 and was a viscous liquid below about 18° C. and a soft, solid gel above about 20° C. The crystalline portion of the liquid suspension settled out of solution when allowed to stand for a day or two at 4° C. or when centrifuged in the cold but could be readily resuspended by mixing while cold. The fact that the suspended material can be sedimented out and resuspended in a smaller volume than the original suspension permits formation of suspensions of significantly higher concentrations, as discussed previously.

In order to determine the solubility of chymotrypsin in the liquid phase of the suspension, aliquots of the total suspension and of the supernatant following centrifugation at 1000–5000 rpm for 5 minutes at 4° C. were assayed spectrophotometrically for enzyme activity. The concentration of chymotrypsin that remained soluble in the Pluronic® F-127 is shown below in Table 2.

TABLE 2

| Enzyme | Solubility (mg/mL)[1] | Std. Dev. |
|---|---|---|
| Chymotrypsin | 0.13[2] | 0.06[2] |

[1]Determined by dividing the activity measured in the supernatant by the calculated activity per mg of protein in the whole suspension.
[2]n = 3.

b) Suspended Enzyme Exhibits Native-like Secondary Structure as Measured by FTIR Infrared spectra obtained using a Nicolet Magna-IR 550 Spectrophotometer in a temperature regulated, 6 μM path length cell were used to examine and compare the structure of chymotrypsin in phosphate buffer (30 mM, pH 7.4) and in 22 percent (w/w) Pluronic® F-127 in the same buffer. Protein concentration in these studies was 20 mg/mL. Careful examination of the spectra showed that the secondary structure of the chymotrypsin was not altered due to suspending the protein in the Pluronic® F-127. Additional FTIR spectroscopic examinations of the structure of chymotrypsin in Pluronic® F-127 at temperatures below and above the gel transition (about 15° C. to 18° C.) showed that the formation of the gel did not alter the structure.

c) Suspended Enzyme Maintains Biological Activity

For this experiment, a chymotrypsin suspension in 22 percent Pluronic® F-127 was prepared as described above but at two different concentrations, 20 mg/mL and 2 mg/mL. Solutions with the same protein concentrations were prepared using phosphate buffer (30 mM, pH 7.4) with no Pluronic® F-127. Aliquots of each of these were diluted as necessary and assayed for enzymatic activity as described above. As can be seen from Table 3, below, enzyme incorporated into the gels could be recovered quantitatively and with no loss of activity after the gels were dissolved in buffer.

TABLE 3

| Environment | Concentration (mg/ml) | Dilution before Assay | Observed Activity | Std. Dev. | Percent of Activity in Buffer |
|---|---|---|---|---|---|
| Buffer[1] | 20 | 5000 | 21.2[3,4] | 1.1[3,4] | |
| Pluronic[2] | 20 | 5000 | 21.6 | 3.4 | 102 |
| Buffer | 2 | 500 | 21.0 | 0.8 | |
| Pluronic | 2 | 500 | 25.8 | 1.4 | 123 |

[1]Phosphate, 30 mM, pH 7.4
[2]22% (w/w) in 30 mM Phosphate buffer, pH 7.4
[3]Expressed as mAU/min at 410 nm
[4]n = 9

The biological activity of chymotrypsin was not damaged by inclusion in the Pluronic® F-127. A slight enhancement of activity was observed when low levels of the detergent were present in the enzyme assay mixtures. It is possible that the difference in percent recovery observed between the 2 mg/mL and 20 mg/mL samples shown in Table 3 is due to the greater dilution of the gel in the 20 mg/mL sample and thus higher levels of Pluronic® F-127 in the 2 mg/mL samples.

d) Suspended Enzyme Displays Increased Storage Stability

In order to demonstrate that suspending proteins in 22 percent Pluronic® F-127 has a stabilizing action, 20 mg/mL chymotrypsin was prepared in either 30 mM phosphate buffer, pH 7.4 or 22 percent Pluronic® F-127 in this buffer as described above. These suspensions were diluted as necessary and enzyme activity was assayed. The results shown in Table 4 below, demonstrate that the enzyme incubated in the presence of Pluronic® F-127 retained more activity than enzyme incubated in the presence of phosphate buffer alone.

TABLE 4

| Time (hr.) | Buffer[1] 8 degrees | Pluronic[2] 8 degrees | Buffer 25 degrees | Pluronic 25 degrees | Buffer 37 degrees | Pluronic 37 degrees |
|---|---|---|---|---|---|---|
| 1 | 100[3] | 100 | 100 | 100 | 100 | 100 |
| 24 | 104 | 79 | 104 | 84 | na[4] | 59 |
| 48 | 94 | 98 | 86 | 82 | 15 | 46 |
| 94 | 105 | 96 | 7 | 65 | 2 | 7 |

[1]Phosphate
[2]22% (w/w) in phosphate buffer, 30 mM, pH 7.4
[3]Expressed as a percentage of the 1 hour value
[4]Value not available Thus, Pluronic® F-127 provides a stabilizing environment, which is more evident at extended times and elevated temperatures, in which peptide and protein containing drugs may be suspended prior to and during delivery. Additionally, other protein stabilizing agents may be added to the formulation as described further in Example 6 below.

EXAMPLE 2

Preparation and Characterization of a Suspension of Subtilisin in Pluronic® F-127 a) Preparation of the Suspension

A suspension of subtilisin was made by the same procedure described in detail above for chymotrypsin. The physical properties were the same in terms of formation and behavior of the milky white suspension and gel-sol transition temperature. The solubility of subtilisin in the liquid phase of the suspension was examined using the method described above and found to be different as might be expected for a different protein. The results are represented in Table 5 below.

TABLE 5

| Enzyme | Solubility (mg/mL)[1] | Std. Dev. |
|---|---|---|
| Subtilisin | 6.48[2] | 1.11[2] |

[1]Determined by dividing the activity measured in the supernatant by the calculated activity per mg of protein in the whole suspension
[2]n = 2 b) Suspended Enzyme Exhibits Native-like Secondary Structure as Measured by FTIR Subtilisin suspensions, like those of chymotrypsin described above, were examined by FTIR spectroscopy to determine whether inclusion in the gel had any effect on the structure and whether the gel-sol transition influenced structure. As in the case of chymotrypsin, there was no effect on structure.

c) Suspended Enzyme Maintains Biological Activity

In experiments similar to those described above for chymotrypsin, subtilisin suspensions were prepared in both phosphate buffer and 22 percent Pluronic® F-127 in phosphate buffer and then dissolved by dilution with buffer. In these cases like in the case of chymotrypsin, 100 percent of the enzyme activity was recovered showing that biological activity was stable while incorporated into the gel suspension.

d) Suspended Enzyme Displays Increased Storage Stability

In order to demonstrate that suspending subtilisin in 22 percent Pluronic® F-127 has a stabilizing action similar to that demonstrated for chymotrypsin, 20 mg/mL subtilisin was prepared in either 30 mM phosphate buffer, pH 7.4 or 22 percent Pluronic® F-127 in phosphate buffer as described above. These suspensions were incubated at temperatures of 8, 25 and 37° C. for times up to 118 hours, the gels or suspensions were diluted as necessary and enzyme activity was assayed. The results, shown below in Table 6, demonstrate that even though subtilisin is autocatalytic and looses activity more rapidly than chymotrypsin, it still retained more activity when incubated in the presence of Pluronic® F-127 than when incubated in the presence of phosphate buffer alone.

TABLE 6

| Time (hr.) | Buffer[1] 8 degrees | Pluronic[2] 8 degrees | Buffer 25 degrees | Pluronic 25 degrees | Buffer 37 degrees | Pluronic 37 degrees |
|---|---|---|---|---|---|---|
| 0.5 | 100[3] | 100 | 100 | 100 | 100 | 100 |
| 24 | 55 | 54 | 32 | 45 | 14 | 23 |
| 48 | 62 | 72 | 35 | 40 | 8 | 15 |
| 118 | 57 | 80 | 14 | 25 | 2 | 4 |

[1]Phosphate, 30 mM, pH 7.4
[2]22% (w/w) in phosphate buffer, 30 mM, pH 7.4
[3]Expressed as a percentage of the 0.5 hour value

EXAMPLE 3

Preparation and Characterization of a Suspension of Lactate Dehydrogenase in Pluronic® F-127 a) Preparation of the Suspension

A suspension of lactate dehydrogenase was made by the same procedure described in detail above for chymotrypsin. Visual observations indicated that the physical properties were the same in terms of formation and behavior of the milky white suspension and gel-sol transition temperature.

b) Suspended Enzyme Maintains Biological Activity

In experiments similar to those described above for chymotrypsin, lactate dehydrogenase suspensions were prepared in both phosphate buffer and 22 percent Pluronic® F-127 in phosphate buffer and then dissolved by dilution with buffer. In these cases like in the case of chymotrypsin, 100 percent of the enzyme activity was recovered showing that biological activity was stable while incorporated into the gel suspension.

c) Suspended Enzyme Displays Increased Storage Stability

Experiments like those carried out with chymotrypsin were conducted to illustrate the effect of Pluronic® F-127 in stabilizing the enzyme activity of lactate dehydrogenase during storage at elevated temperatures. In this case 0.5 M sucrose was included in some samples and thus it was necessary to reduce the concentration of Pluronic® F-127 to 18 percent to maintain the same gel-sol transition temperature. Table 7 below, shows the results obtained when lactate dehydrogenase was stored for 48 hours at 37° C.

TABLE 7

| Sample Composition[1] | Enzyme Activity[2] | Std. Dev. (n = 3) |
|---|---|---|
| 18% Pluronic | 59.3 | 1.7 |
| 18% Pluronic + 0.5 M sucrose | 46.1 | 2.7 |
| 0.5 M sucrose | 39.1 | 3.3 |
| buffer alone | 40.0 | 1.7 |

[1]Buffer used in all was 50 mM Tris:HCl, pH 7.35 with 0.1% NaN$_3$
[2]Expressed in arbitrary units

EXAMPLE 4

Preparation and Characterization of a Suspension of Bovine Serum Albumin in Pluronic® F-127 a) Preparation of the Suspension

Several mixtures of Pluronic® F-127 and bovine serum albumin were made in attempts to find a combination that would be a clear gel with a protein concentration of 15 mg/mL or higher at room temperature. Pluronic® F-127 concentrations below 20 percent (w/w) would not gel at 25° C. or below and concentrations of 20 percent and above resulted in the milky, white suspension when bovine serum albumin was added at concentrations of 14 mg/mL and above. Thus, no combination was found that would provide the desired properties. Subsequent studies of structure and stability on several proteins demonstrated that it was not necessary to have a clear gel to have a satisfactory protein drug delivery formulation with Pluronic® F-127.

b) Suspended Protein Exhibits Native-like Secondary Structure as Measured by FTIR Preliminary FTIR spectroscopic examination of the structure of a suspension of 20 mg/mL bovine serum albumin in 22 percent Pluronic® F-127 showed no differences from a similar suspension of the protein in buffer alone. This result was similar to results from more extensive examinations of the structures of chymotrypsin and subtilisin suspended in the gel.

EXAMPLE 5

Preparation and Characterization of a Suspension of Insulin in Pluronic® F-127 a) Preparation of the Suspension

A suspension of insulin was made by the same procedure described in detail above for chymotrypsin. Visual observation indicated that the physical properties were the same in terms of formation and behavior of the milky white suspension and gel-sol transition temperature.

b) Suspended Protein Exhibits Native-like Secondary Structure as Measured by FTIR Insulin suspensions, like those of chymotrypsin described above, were examined by FTIR spectroscopy to determine whether inclusion in the gel had any effect on the structure and whether the gel-sol transition influenced structure. As in the case of chymotrypsin, there was no effect on structure.

EXAMPLE 6

Protein Stabilizing Agents Used to Manipulate Gel Properties

Various concentrations of sucrose were incorporated into Pluronic® F-127 solutions as an example of the use of known protein stabilizing agents to manipulate the properties of the gels. Typical results for gel-sol transition temperature are shown in Table 8 below.

TABLE 8

| % Pluronic[1] | 0 M Sucrose | 0.5 M Sucrose | 1.0 M Sucrose | 1.5 M Sucrose |
|---|---|---|---|---|
| 16 |  | 25 | 20 | 0.2 |
| 17 |  | 20 | 14 | −3 |
| 18 |  | 16 | 10 |  |

TABLE 8-continued

| % Pluronic[1] | 0 M Sucrose | 0.5 M Sucrose | 1.0 M Sucrose | 1.5 M Sucrose |
|---|---|---|---|---|
| 20 |  | 22 | 14 |  |
| 22 |  | 18 |  |  |
| 30 |  | 9 |  |  |

[1]w/w, in 30 mM phosphate, pH 7.4

It is clear from Table 8 that the gel-sol transition temperature can be manipulated in the range from below 0° C. to about 25° C. as required by the present invention.

The foregoing description is considered as illustrative only of the principles of the invention. Furthermore, since numerous modifications and changes will readily occur to those skilled in the art, it is not desired to limit the invention to the exact construction and processes shown as described above. Accordingly, all suitable modifications and equivalents may be resorted to falling within the scope of the invention as defined by the claims which follow.

The embodiments of the invention in which an exclusive property or privilege is claimed are defined as follows:

1. A method of varying the liquid-gel transition temperature of a polyoxyalkylene block copolymer having the formula: $HO(C_2H_4O)_b(C_3H_6O)_a(C_2H_4O)_bH$, wherein a is 20 to 80 and b is 15 to 60, the method comprising adding a solute selected from the group consisting of a sugar and a polyether glycol to an aqueous solution of said copolymer so as to increase or decrease said transition temperature.

2. The method of claim 1, wherein said transition temperature is decreased by adding sucrose.

3. The method of claim 1, wherein said transition temperature is increased by adding polyethylene glycol.

4. The method of claim 1 wherein the copolymer has the formula: $HO(CH_2CH_2O)_b(CH_2(CH_3)CHO)_a(CH_2CH_2O)_bH$.

5. The method of claim 4 wherein a is 67 and b is 49.

6. A method of varying the liquid gel transition temperature of a polyoxyalkylene block copolymer comprising adding a solute selected from the group consisting of a sugar and a polyether glycol to an aqueous solution of the copolymer so as to increase or decrease the transition temperature.

7. The method of claim 1 wherein the copolymer is a polyoxyethylene-polyoxypropylene block copolymer.

8. The method of claim 6 wherein the copolymer has the formula:

$$HO(C_2H_4O)_b(C_3H_6O)_a(C_2H_4O)_bH,$$

wherein the polyoxyethylene moiety constitutes at least about 70 percent by weight of said polyoxyalkylene block copolymer, wherein a and b are integers such that the hydrophobe base represented by $(C_3H_6O)_a$ has a molecular weight of at least about 4000, and wherein said copolymer has an average molecular weight of about 12,600.

9. The method of claim 6 wherein the liquid-gel transition temperature is decreased by adding sucrose.

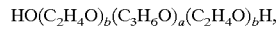

10. The method of claim 6 wherein the liquid-gel transition temperature is increased by adding polyethylene glycol.